United States Patent
Larnard

Patent Number: 5,720,775
Date of Patent: Feb. 24, 1998

[54] PERCUTANEOUS ATRIAL LINE ABLATION CATHETER

[75] Inventor: Donald J. Larnard, Boca Raton, Fla.

[73] Assignee: Cordis Corporation, Miami Lakes, Fla.

[21] Appl. No.: 688,906

[22] Filed: Jul. 31, 1996

[51] Int. Cl.⁶ ............................................. A61N 1/00
[52] U.S. Cl. ................... 607/122; 607/119; 128/642; 606/41
[58] Field of Search ...................... 607/116, 119, 607/122; 128/642; 600/141, 144, 146; 606/32, 41

[56] References Cited

U.S. PATENT DOCUMENTS

| | | |
|---|---|---|
| 4,440,108 | 4/1984 | Little et al. |
| 4,526,637 | 7/1985 | Long |
| 4,565,200 | 1/1986 | Cosman ........................ 606/50 X |
| 4,693,760 | 9/1987 | Sioshansi |
| 4,706,681 | 11/1987 | Breyer et al. |
| 4,743,493 | 5/1988 | Sioshansi et al. |
| 4,855,026 | 8/1989 | Sioshansi |
| 4,968,006 | 11/1990 | Oliver |
| 5,087,243 | 2/1992 | Avitall |
| 5,098,483 | 3/1992 | Little et al. |
| 5,104,690 | 4/1992 | Greenwald |
| 5,118,400 | 6/1992 | Wollam |
| 5,123,924 | 6/1992 | Sioshansi et al. |
| 5,133,757 | 7/1992 | Sioshansi et al. |
| 5,236,413 | 8/1993 | Feiring |
| 5,286,254 | 2/1994 | Shapland |
| 5,323,781 | 6/1994 | Ideker et al. ................ 607/122 |
| 5,411,544 | 5/1995 | Mar et al. ................ 607/122 |
| 5,429,130 | 7/1995 | Goldman |
| 5,462,545 | 10/1995 | Wang et al. ................ 606/48 |
| 5,478,330 | 12/1995 | Imran et al. ................ 607/122 |
| 5,489,270 | 2/1996 | Van Erp |
| 5,545,193 | 8/1996 | Fleischman et al. ................ 128/642 |
| 5,549,661 | 8/1996 | Kordis et al. ................ 607/99 |
| 5,575,810 | 11/1996 | Swanson et al. ................ 128/642 |
| 5,617,854 | 4/1997 | Munsif ................ 606/50 |

FOREIGN PATENT DOCUMENTS

| | | |
|---|---|---|
| 350282 | 7/1989 | European Pat. Off. |
| 499491 | 2/1992 | European Pat. Off. |
| 571797 | 5/1993 | European Pat. Off. |
| 9308869 | 11/1992 | WIPO |
| 9419053 | 1/1994 | WIPO |

OTHER PUBLICATIONS

Biomaterials Surface Engineering Services "Surfaces Engineered for Superior Performance", Spire Corporation.

*Primary Examiner*—Jennifer Bahr
*Assistant Examiner*—David M. Ruddy
*Attorney, Agent, or Firm*—Lockwood, Alex, Fitzgibbon & Cummings

[57] ABSTRACT

A percutaneous line ablation catheter is provided for ablating maze-like patterns on the surface of the heart of a patient through line ablation procedure. Typically, the catheter will include an internal electrode at its distal portion that is rendered electrically conductive by ion process deposition of the polymeric material of its shaft with a metallic material or materials. An external electrode typically will be placed on the outside surface of the patient's body, and a conductive circuit connected between the external electrode and the internal electrode to develop an electrical circuit through the patient's body.

9 Claims, 1 Drawing Sheet

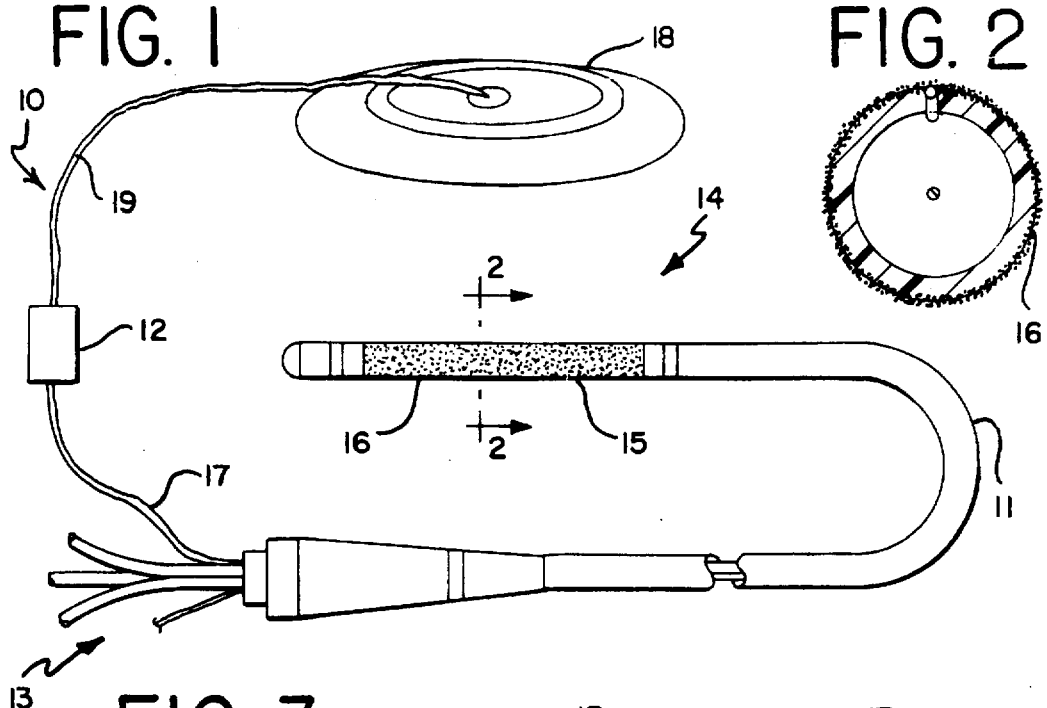
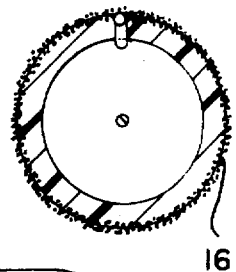
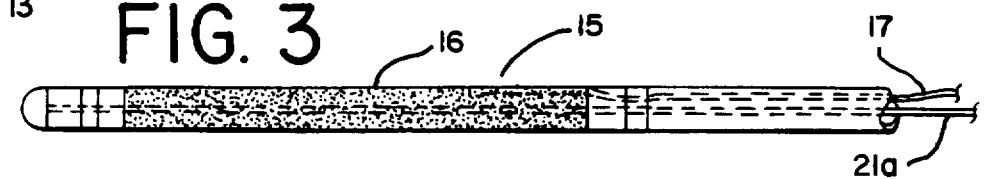
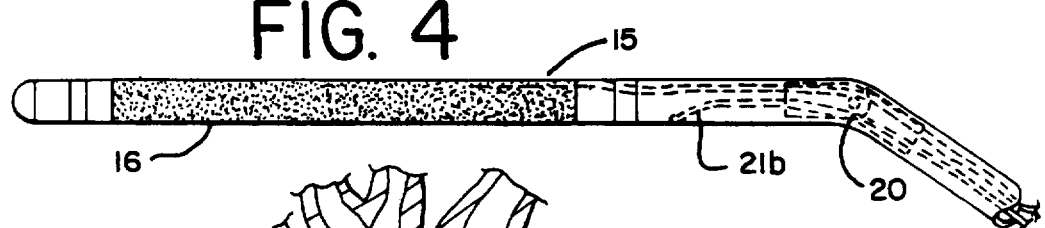
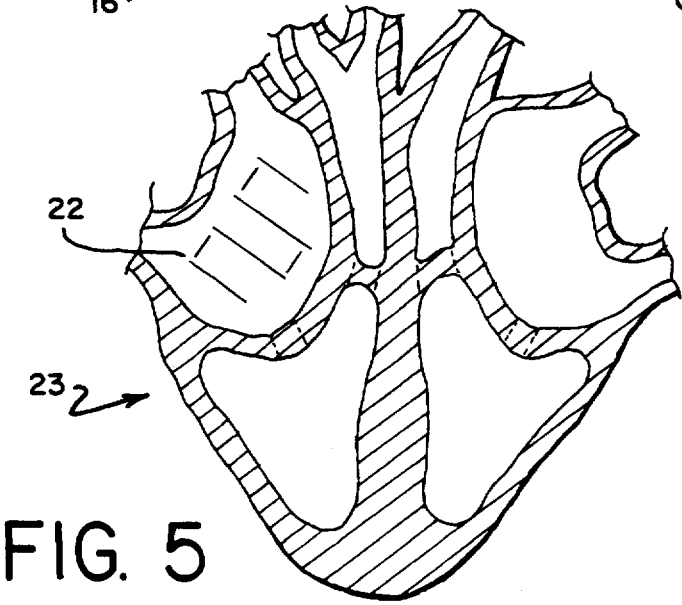
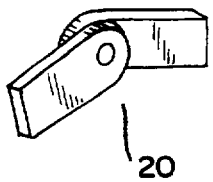

PERCUTANEOUS ATRIAL LINE ABLATION CATHETER

BACKGROUND AND SUMMARY OF THE INVENTION

This invention relates to a percutaneous atrial line ablation catheter having a specially advantageous ablation property. More particularly, this atrial ablation catheter includes the desirable property of line ablation of the inner surface of the heart.

In various atrial arrhythmias such as atrial flutter and atrial fibrillation, ablation of the arrhythmogenic foci or pathways is sometimes difficult due to the lack of a specific single focal site. This problem is particularly complicated in atrial fibrillation instances. In atrial fibrillation, there is usually a fair amount of degenerative muscle disease and fibrous tissue formation thereby changing the electrophysiological properties of the atrial chamber muscle. As a result, different excitation thresholds for the muscle can exist rather than the normal and traditional synchronous muscle contraction with similar excitation thresholds. The result is that many foci in the atria can become excited at different times and synchronous contraction can become the exception rather than the rule.

One approach which has been proposed in order to treat such a condition is a surgical technique. With this technique, heart surgeons cut and almost "fillet" the atrial muscle during an open-heart procedure in order to address aberrant conditions. The cuts made in the heart muscle combine to form an almost maze-like pattern which is in effect a series of lines on the surface of the heart. These line ablations help in abating the problems encountered in atrial fibrillation.

Surgically, in an open-heart procedure, this maze-design line ablation technique can be successful in diminishing and abating atrial fibrillation without causing heart block and rendering the patient pacemaker-dependent. In the past, electrophysiology (E.P.) catheters have been used to accomplish an ablation technique on the inner surface of the heart. If a physician were to attempt a line ablation with such an E.P. catheter, this would require performing point to point ablations on the inner surface of the heart and in effect draw a line ablation by connecting sufficient number of point ablations on this surface. This point ablation procedure can be impractical, time consuming and costly.

A typical catheter can include one or more electrodes, such as a band or ring electrode and a tip electrode. Electrodes of this type will be in engagement with the body tissue to be treated or diagnosed, such as an internal surface of the heart of a patient. In the past, catheters with elongated electrodes made of a series of conductive ring electrodes on the elongated electrode have been proposed. Such an elongated electrode could be dragged on the surface of the tissue for ablation purposes.

Accordingly, the present invention recognizes that it is desirable to perform a line ablation or a maze-design line ablation technique percutaneously and without the necessity of resorting to a point ablation technique. This is accomplished using the percutaneous atrial line ablation catheter and technique of the present invention.

In accordance with this invention, a line ablation catheter is provided which has a distal portion with a metallic coating on it which is an elongated conductive electrode that is soft and pliable as needed. This distal portion is bendable at a desired angle without excessive flexing or curving of the distal end. The procedure and catheter according to the invention exhibits improved characteristics over prior art catheters, particularly by achieving the advantageous line ablation procedure without requiring a point ablation procedure or open heart surgery.

It is a general object of the present invention to provide an improved line ablation catheter and method of using same.

Another object of the present invention is to provide an improved line ablation catheter for percutaneously ablating the inner surface of the atrium of the heart.

Another object of the present invention is to provide an improved line ablation catheter which includes an elongated conductive electrode for percutaneously ablating internal body tissues, such as the endocardial surface of the atrium.

Another object of the present invention is to provide an improved line ablation catheter which includes a bending joint for flexibly bending and directing the distal portion of the catheter having an elongated conductive electrode, in order to contact and ablate the body tissues in a maze-design pattern.

BRIEF DESCRIPTION OF THE DRAWING

The invention will be further elucidated in the following description with reference to the drawings in which:

FIG. 1 is an elevational view, partially broken away, of a preferred percutaneous line ablation catheter system and circuit in accordance with the present invention;

FIG. 2 is a cross-sectional view along the line 2—2 of the elongated electrode of the percutaneous line ablation catheter in accordance with the present invention;

FIG. 3 is a detailed view of a first embodiment of the percutaneous line ablation catheter in accordance with the present invention, illustrating the distal portion of the catheter shown in FIG. 1;

FIG. 4 is a detailed view similar to FIG. 3 and depicting a second embodiment of the percutaneous line ablation catheter in accordance with the present invention;

FIG. 5 is an illustration of a line ablation which can be carried out accordance with the present invention; and FIG. 6 is a detailed view of the bending joint used in the second embodiment of the percutaneous line ablation catheter in accordance with the present invention.

DESCRIPTION OF THE PARTICULAR EMBODIMENTS

An illustration of a percutaneous atrial line ablation catheter that incorporates the present invention is generally designated as 10 in FIG. 1. The percutaneous line ablation catheter 10 includes an elongated shaft generally designated as 11. The illustrated line ablation catheter 10 further includes a proximal portion 13, and a distal portion 14. As further illustrated in FIG. 1, the distal portion 14 includes an elongated electrically conductive electrode coating 15.

When in use as a component of a double-polar line ablation catheter system, the catheter 10 is in electrical communication with an external conductive electrode 18 which is positioned on a surface outside of the body of the patient. Typically this system or circuit will include an electrical energy source 12 which is hard-wired to the catheter 10 and external electrode 18 by means of an external conduction wire 19.

A typical use of the present invention is in endocardial electrical procedures. A puncture is made in a patient, for example in the groin area. The line ablation catheter is inserted inside the incision and into the blood vessel or the like. It will be appreciated by those skilled in the art that the puncture could be made in other areas of the body in order to gain access to the desired body cavity and/or body organ. The catheter is thus within the patient's body, and it is guided within the body vessel as desired.

More specifically, the catheter with an electrically conductive electrode is directed manually up through the patient's abdomen and thorax until it is in contact with the inside surface of the heart.

More particular reference is now made to the embodiments of the line ablation catheter 10 which are illustrated in FIGS. 3 and 4. The elongated electrode 15 is a polymeric cylinder which has been rendered electrically conductive by adding a metallic component to it. In the embodiments illustrated in the drawings, the metallic component takes the form of an extremely thin adherent film of metallic material 16. In the illustrated embodiments, this metallic material 16 is a coating which provides an external conductive surface (FIG. 2). This electrically conductive surface transforms the distal portion 14 of the elongated shaft 11 into an electrode which is required for carrying out the procedures discussed herein.

It is necessary to provide secure electrical communication between the elongated electrically conductive electrode 15 and the electrical energy source 12. As illustrated in FIG. 3, the first embodiment of the present invention, electrical communication is achieved by incorporating a conductive wire 17 within the elongated shaft 11 and making an electrical connection between the metallic material 16 and the conductive wire 17. Wire 17 then runs to the electrical energy source 12. Thus, a circuit can be provided between external conductive electrode 18 and the electrode 16 of the catheter which circuit includes the electrical energy source 12, the conductive wire 17 and the external conductive wire 19 (see FIG. 1).

As electrical energy is applied to the line ablation catheter 10, an electrical circuit is completed through the patient's body. The elongated conductive electrode 15 will have a potential thereon. The external conductive electrode 18 will have a different potential such as ground. The energy source 12 supplies a Radio Frequency (RF) current to the elongated conductive electrode 15 through the conductive wire 17. It should be appreciated that the patient's body acts as a conductor between the elongated electrode 15 and the external conductive electrode 18. As it is old and known, an electrical circuit is always completed through a path of least resistance. In this case, patient's body tissues in contact with the elongated conductive electrode 15 provide this electrical path.

The line ablation catheter of the first illustrated embodiment can be directed within the inner heart by pulling on a pull wire 21a. Such pulling will help to bend the catheter so, for example, the distal portion 14 is at an acute angle with respect to the proximal portion. As the tissues of the inner heart come into engagement with the elongated conductive electrode 15, they are ablated at the areas of contact. Since the elongated electrode 15 is in the form of a tubular elongated metallic cylinder, the resulting ablation is in the shape of a line. Hence, line ablation is effected through the foregoing procedure.

The second embodiment of the present invention is more particularly illustrated in FIG. 4. As shown, a small mechanical joint 20, as shown in more detail in FIG. 6, is positioned inside of the elongated shaft 11 at the distal portion 14 of the line ablation catheter 10, just proximal to the conductive metallic material 16. The catheter will bend at this mechanical joint, especially when such bending is initiated by a pull wire. The illustrated pull wire 21b extends from the proximal end of the catheter to a position closely distal of the mechanical joint 20. In an alternative aspect of this embodiment, the pull wire 21b can extend for the full length of the catheter 10 from the distal end to at or near the proximal end outside the catheter 10.

As illustrated in FIG. 5, the line ablation catheter of the present invention can be used to maneuver the elongated conductive electrode 15 into engagement with the inner surface of the atrium 23 of the heart of the patient being treated. As the elongated conductive electrode 15 contacts the inner surface of the atrium, a line is ablated into the tissue. By further maneuvering the elongated conductive electrode 15 to a different position, for instance a perpendicular or an offset angle orientation in relation to the initial ablated line, an additional line can be ablated on the tissue. This procedure can be repeated until a maze-like pattern 22 is ablated on the tissue.

A typical polymer out of which the distal portion of the elongated shaft will be made is somewhat flexible but yet has adequate rigidity to perform as needed to have the distal electrode 15 lie substantially along a straight line. Typical catheter materials which can be formulated to provide the desired flexibility and strength are polyurethanes, polyethylenes, nylons including polyamide homopolymers and polyamide copolymers, and Teflon compounds.

The conductive surface of extremely thin film of metallic material 16 is preferably applied by ion process deposition of a metal element, metal alloy or metal compound onto the surface of the distal portion polymer to form the elongated electrode 15. The conductive surface should remain malleable enough to withstand flexing of the shaft without flaking off from the shaft. It is important that the metallic material be spread over an elongated surface area inasmuch as an enhanced surface area decreases impedance.

Furthermore, it is important for the elongated electrode 15 to have sufficient stiffness characteristic greater than that of the remainder of the elongated shaft 11 so that it can maintain a substantially straight line shape. In order to achieve a sufficient stiffness of the elongated electrode 15, a controlled amount of metallic material 16 can be adhered to the surface of the elongated electrode 15 such that the elongated shaft 11 bends or flexes and it does not deflect in a curved manner when it is manipulated through the pull wires 21a or 21b by the physician.

An example of a suitable ion process deposition of the metallic material is one available from Spire Corporation, of Bedford, Mass. Some such processes are identified as SPI-ARGENT and SPI-MET (trademarks) procedures. Such are especially suitable for metallizing polymeric surfaces and can provide the desired thin film of metallic material that is characteristic of the present invention. The basic procedure is one of ion process deposition.

Generally speaking, processes suitable for the present invention can be characterized as achieving chemical vapor deposition. A rastered ion beam of a suitable chemical can also be applied such that the metallic material is "pounded" and bonded into the polymer by being bombarded by the ion beam. The result is a very thin, highly adherent metallic material film that is both mechanically and chemically bonded to the polymeric catheter shaft. Surface area enlargement or enhancement can also be achieved by further raster ion beam bombardment in order to "dimple" or texture the deposited metallic material surface. An example is the SPI-TEXT (trademark) process of Spire Corporation.

Patents which disclose these procedures and related equipment and specific materials and processing conditions include U.S. Pat. Nos. 4,229,232, 4,443,488, 4,693,760, 4,743,493, 5,104,690, 5,118,400, 5,123,924, 5,133,757 and 5,236,509. These disclosures are incorporated by reference hereinto.

It will be appreciated that, if the metallic material film is too thick, it will rigidify the polymeric cylinder too severely, and it will lose the flexibility and feel normally associated with catheter shafts. If the metallic material does not adhere adequately and merely encapsulates the polymeric surface, rather than being bonded to it and into it, delamination can be a problem. Also, a very thin material which is well bonded to and into the surface of the polymeric material will run substantially no risk of interfering with or "catching" during catheter delivery and manipulation. The metallic material coating does not significantly negatively modify the mechanical properties of the catheter shaft and in fact can enhance mechanical tear and puncture resistance properties.

A suitable very thin, highly adherent metallic material coating will be not greater than about 10 microns in thickness, preferably not greater than about 5 microns. A suitable exemplary thickness is about 1 to 4 microns. Either a single metal, metal alloy or metal compound deposition or a multiple metallic material deposition can be carried out. For example, some metallic materials have especially high conductivity or low resistivity while others, although having suitable electrical properties, are particularly well suited because of especially high biocompatibility or inertness within an in vivo setting, making them especially advantageous as an external coating.

It has been found that the conducting metallic material should have a resistivity of equal to or less than about 50 microhm-centimeters at 20° C. The metallic materials should also be biocompatible. Examples of materials that meet these resistivity and biocompatibility criteria include gold, Monel metal alloy, platinum, silver, steel alloys such as stainless steel, tantalum, titanium and titanium nitride. Generally, metallic materials suitable for use as pacemaker electrodes or as ablation electrodes should meet the criteria for the metallic material of the present invention.

The following is a listing of metallic elements or metallic alloys that exhibit the desired resistivity and theoretical resistance discussed herein. These data are theoretical resistance calculations for selected conductors. The segment length used was 10.8 cm, and the size used was 8 French, its outer diameter being 0.2667 cm. These resistivity and resistance calculations are as follows:

| Metallic Material | Coating and Thickness | Resistivity at 20° C. (Microhms-cm) | Cannula Theoretical Resistance at 37° C. (ohms) |
|---|---|---|---|
| gold | 3 | 2.44 | 1.37 |
| gold | 4 | 2.44 | 0.10 |
| Monel metal | 3 | 42 | 19.38 |
| Monel metal | 4 | 42 | 1.45 |
| platinum | 3 | 10.6 | 5.22 |
| platinum | 4 | 10.6 | 0.39 |
| silver | 3 | 1.59 | 0.84 |
| silver | 4 | 1.59 | 0.06 |
| steel (E.B.B) | 3 | 10.4 | 5.29 |
| steel (E.B.B) | 4 | 10.4 | 0.40 |
| tantalum | 3 | 15.5 | 7.42 |
| tantalum | 4 | 15.5 | 0.56 |
| titanium | 3 | 42 | 18.05 |
| titanium | 4 | 42 | 1.35 |

In an exemplary procedure, silver metal is deposited by the Spire process to 3000 angstroms in thickness. Resistance is measured to be in the range of about 1 ohm, which generally corresponds to these data. For example, titanium deposited to a thickness of about 4 microns should show the resistance of the shaft to be on the order of 1.35 ohm. In other examples, titanium is deposited to a thickness of 500 angstroms, and titanium nitride can be also suitably deposited. Desirably, the resistance of the electrode at body temperature, 37° C., should be on the order of about 1 ohm or less. This resistance should occur for coating thicknesses of less than 10 microns, including those as thin as 3 or 4 microns, or less, as illustrated by the above data. Measured DC resistance should be 10 ohms or less, at 37° C.

In an especially preferred arrangement, a PEBAX 70D polymeric cylinder is subjected to ion process deposition of silver. This provides a base coating which is extremely electrically conductive. This is followed by ion process deposition of gold metal thereunto in order to enhance the inertness of the metallic material deposition to the body. The total metallic material thus coated has a thickness of approximately 2 microns. Typical shaft sizes are on the order of 6 French, 7 French and 8 French.

It will be understood that the embodiments of the present invention which have been described are illustrative of some of the applications of the principles of the present invention. Various modifications may be made by those skilled in the art without departing from the true spirit and scope of the invention.

I claim:

1. A catheter for percutaneous in vivo ablation of atrial muscle of a patient, comprising:

an elongated catheter body being a tube having a proximal end portion and a distal end portion, said distal end portion having an external treatment surface;

a mechanical bending joint positioned inside said elongated catheter body, said mechanical bending joint generally defining a distal end of the proximal end portion and a proximal end of the distal end portion;

said external treatment surface having an elongated metallic coating extending throughout a majority of the length of said distal end portion and from the distal tip of the catheter to a location closely distal of the mechanical bending joint, said elongated metallic coating being an ion deposition of a metallic material onto said distal end portion of the catheter tube;

a conductive circuit between said elongated metallic coating and a source of electrical energy which is external of the patient;

a deflection assembly for directing and manipulating said external treatment surface to define an elongated line of contact which, upon activation of the source of electrical energy, ablates an elongated ablation line, said deflection assembly includes said mechanical bending joint including at least two pivotally connected hinge members and a pull wire secured to the distal end portion at a location closely distal of said mechanical bending joint; and said external treatment surface is a straight-line surface adapted to engage and ablate the elongated ablation line into an atrial muscle of a patient.

2. The catheter according to claim 1, wherein said deflection assembly includes a pull wire extending from the proximal end portion to said distal end portion.

3. The catheter according to claim 1, wherein the portion of the tube having said external treatment surface has a stiffness such that said external treatment surface maintains a substantially straight line-shape generally along the length of the metallic coating and bends in relation to the remaining portion of the catheter at a position closely proximal to said external treatment surface.

4. The catheter according to claim 2, wherein said deflection assembly further includes a bending joint positioned closely proximal to said metallic coating.

5. The catheter according to claim 1, wherein said conductive circuit includes an external electrode.

6. A catheter for percutaneous in vivo ablation of atrial muscle of a patient, comprising:

an elongated catheter body being a tube having a proximal end portion and a distal end portion with an external treatment surface;

a mechanical bending joint positioned inside said elongated catheter body, said mechanical bending joint generally defining a distal end of the proximal end portion and a proximal end of the distal end portion;

said external treatment surface having an elongated metallic coating extending through a majority of the length of said distal end portion and from the distal tip of the catheter to a location closely distal of the mechanical bending joint, said elongated metallic coating being an ion deposition of a metallic material onto and into said distal end portion of the catheter tube;

a deflection assembly including said mechanical bending joint and a pull wire secured to the distal end portion at a location closely distal of said bending joint, said bending joint including at least two pivotally connected hinge members;

a conductive circuit between said metallic coating and a source of electrical energy which is external of the patient; and the portion of the tube having said external treatment surface has a stiffness such that said external treatment surface maintains a substantially straight-line shape generally along the length of the metallic coating, and said catheter body bends at said bending joint, in response to pulling on said pull wire, said catheter thereby being adapted to engage an atrial muscle of a patient along an elongated line of contact which, upon activation of the source of electrical energy, is adapted to ablate an elongated ablation line into the atrial muscle.

7. The catheter according to claim 6, wherein said conductive circuit includes an external electrode.

8. A catheter for percutaneous in vivo ablation of atrial muscle of a patient, comprising:

an elongated catheter body being a tube having a proximal end portion and a distal end portion which extends from the distal tip of the catheter to a bending location along the catheter body, said distal end portion having an external treatment surface;

said external treatment surface having an elongated metallic coating extending through a majority of the length of said distal end portion;

a conductive circuit between said metallic coating and a source of electrical energy which is external of the patient;

a deflection assembly adapted to bend said catheter at the bending location and thereby adapted to engage said external treatment surface with an atrial muscle along an elongated line of contact which, upon activation of the source of electrical energy, is adapted to ablate an elongated ablation line into the atrial muscle; and said metallic coating is a multiple-layered ion process deposition including a deposition of silver bonded to said elongated catheter body and a deposition of gold thereonto.

9. The catheter of claim 8, wherein said deflection assembly includes a mechanical bending joint positioned closely proximal to said metallic coating and a pull wire secured to the distal end portion at a location closely distal of said mechanical bending joint, said mechanical bending joint including at least two pivotally connected hinge members.

* * * * *

UNITED STATES PATENT AND TRADEMARK OFFICE
CERTIFICATE OF CORRECTION

PATENT NO.　：　5,720,775
DATED　　　：　February 24, 1998
INVENTOR(S)：　Donald J. Larnard It is certified that error appears in the above-indentified patent and that said Letters Patent is hereby corrected as shown below:

```
Col. 2, line 23, "BRIEF DESCRIPTION OF THE DRAWING" should read
     --BRIEF DESCRIPTION OF THE DRAWINGS--; line 41, "out
     accordance" should read --out in accordance--.
Col. 5, line 29, "in vivo" should be in italics.
Col. 6, line 24, "of applications" should read --of the
     applications--; line 29, "in vivo" should be in italics.
Col. 7, line 9, "in vivo" should be in italics.
Col. 8, line 8, "in vivo" should be in italics.
```

Signed and Sealed this

Fifteenth Day of December, 1998

Attest:

Attesting Officer

BRUCE LEHMAN

Commissioner of Patents and Trademarks